(12) United States Patent
Herrington

(10) Patent No.: US 7,008,523 B2
(45) Date of Patent: Mar. 7, 2006

(54) ELECTROLYTIC CELL FOR SURFACE AND POINT OF USE DISINFECTION

(75) Inventor: Rodney E. Herrington, Albuquerque, NM (US)

(73) Assignee: MIOX Corporation, Albuquerque, NM (US)

( * ) Notice: Subject to any disclaimer, the term of this patent is extended or adjusted under 35 U.S.C. 154(b) by 0 days.

(21) Appl. No.: 10/785,610

(22) Filed: Feb. 23, 2004

(65) Prior Publication Data
US 2004/0211676 A1 Oct. 28, 2004

Related U.S. Application Data

(63) Continuation-in-part of application No. 09/907,092, filed on Jul. 16, 2001, now Pat. No. 6,736,966.

(60) Provisional application No. 60/448,994, filed on Feb. 21, 2003.

(51) Int. Cl.
C02F 1/461 (2006.01)

(52) U.S. Cl. .................. 205/701; 205/742; 205/755; 204/232; 204/271; 204/275.1

(58) Field of Classification Search ............... 205/701, 205/742, 755; 204/232, 271, 275.1
See application file for complete search history.

(56) References Cited

U.S. PATENT DOCUMENTS

| | | |
|---|---|---|
| 1,029,580 A | 6/1912 | Bane |
| 1,200,165 A | 10/1916 | Burgess |
| 2,473,986 A | 6/1949 | Booth |
| 3,222,269 A | 12/1965 | Stanton |
| 3,234,110 A | 2/1966 | Beer |
| 3,365,061 A | 1/1968 | Bray |
| 3,505,215 A | 4/1970 | Bray |
| 3,622,479 A | 11/1971 | Schneider |
| 3,654,148 A | 4/1972 | Bradley |
| 3,749,524 A | 7/1973 | Jordan |
| 3,791,768 A | 2/1974 | Wanner |
| 3,825,122 A | 7/1974 | Taylor |
| 3,996,126 A | 12/1976 | Rasmussen |
| 4,000,065 A | 12/1976 | Ladha et al. |
| 4,019,986 A | 4/1977 | Burris et al. |
| 4,070,280 A | 1/1978 | Bray |
| 4,077,883 A | 3/1978 | Bray |
| 4,124,488 A | 11/1978 | Wilson |
| 4,151,092 A | 4/1979 | Grimm et al. |
| 4,187,173 A | 2/1980 | Keefer |
| 4,288,326 A | 9/1981 | Keefer |
| 4,290,873 A | 9/1981 | Weaver |
| 4,306,952 A | 12/1981 | Jansen |
| 4,321,137 A | 3/1982 | Kohler |

(Continued)

OTHER PUBLICATIONS

Advertisement for "Steri-Pen" device marketed by Hydro-Photon, Inc. on web site located at 222.hydro-photon.com.

(Continued)

*Primary Examiner*—Arun S. Phasge
(74) *Attorney, Agent, or Firm*—Deborah A. Peacock; Philip D. Askenazy; Peacock Myers, P.C.

(57) ABSTRACT

The present invention is an apparatus and method for disinfecting or sanitizing a desired object. The apparatus includes a container for an aqueous solution; the container may be a spray bottle. The apparatus includes an electrolytic cell, containing an electrolyte, an electrical power source, a control circuit for providing an electric charge to the electrolyte to create an oxidant, and a fluid connection between the cell and container to permit introduction of the oxidant into the aqueous solution to create a disinfectant.

39 Claims, 3 Drawing Sheets

U.S. PATENT DOCUMENTS

| | | |
|---|---|---|
| 4,367,140 A | 1/1983 | Wilson |
| 4,389,311 A | 6/1983 | La Freniere |
| 4,432,876 A | 2/1984 | Keefer |
| 4,434,056 A | 2/1984 | Keefer |
| 4,496,443 A | 1/1985 | Mack et al. |
| 4,534,713 A | 8/1985 | Wanner |
| 4,560,455 A | 12/1985 | Porta et al. |
| RE32,077 E | 2/1986 | deNora et al. |
| RE32,144 E | 5/1986 | Keefer |
| 4,632,754 A | 12/1986 | Wood |
| 4,722,263 A | 2/1988 | Valentin |
| 4,724,079 A | 2/1988 | Sale et al. |
| 4,744,877 A | 5/1988 | Maddock |
| 4,756,830 A | 7/1988 | Fredkin |
| 4,759,844 A | 7/1988 | Lipschultz et al. |
| 4,761,208 A | 8/1988 | Gram et al. |
| 4,786,380 A | 11/1988 | Van Duin et al. |
| 4,790,923 A | 12/1988 | Stillman |
| 4,790,946 A | 12/1988 | Jansen |
| 4,836,924 A | 6/1989 | Solomon |
| RE33,135 E | 12/1989 | Wanner, Sr. al. |
| 4,973,408 A | 11/1990 | Keefer |
| 4,976,842 A | 12/1990 | Fowler |
| 5,085,753 A | 2/1992 | Sherman |
| 5,207,916 A | 5/1993 | Goheen et al. |
| 5,244,579 A | 9/1993 | Horner et al. |
| 5,306,428 A | 4/1994 | Tonner |
| 5,320,718 A | 6/1994 | Molter et al. |
| 5,358,635 A | 10/1994 | Frank et al. |
| 5,385,711 A | 1/1995 | Baker et al. |
| 5,480,386 A | 1/1996 | Brohy et al. |
| 5,492,534 A | 2/1996 | Athayde et al. |
| 5,496,466 A | 3/1996 | Gray |
| 5,503,736 A | 4/1996 | Schoenmeyr |
| 5,531,887 A | 7/1996 | Miers |
| 5,534,145 A | 7/1996 | Platter et al. |
| 5,540,848 A | 7/1996 | Engelhard |
| 5,558,762 A | 9/1996 | Fife et al. |
| 5,581,189 A | 12/1996 | Brenn |
| 5,597,482 A | 1/1997 | Melyon |
| 5,685,980 A | 11/1997 | Patapoff et al. |
| 5,725,758 A | 3/1998 | Chace et al. |
| 5,795,459 A | 8/1998 | Sweeney |
| 5,858,201 A * | 1/1999 | Otsuka et al. ............... 205/701 |
| 5,900,212 A | 5/1999 | Maiden et al. |
| 5,911,870 A | 6/1999 | Hough |
| 5,928,490 A | 7/1999 | Sweeney |
| 5,958,229 A | 9/1999 | Filiopoulos et al. |
| 5,989,396 A | 11/1999 | Prasnikar et al. |
| 6,007,686 A | 12/1999 | Welch et al. |
| 6,110,424 A | 8/2000 | Maiden et al. |
| 6,180,014 B1 | 1/2001 | Salama |
| 6,309,523 B1 | 10/2001 | Prasnikar et al. |
| 6,363,951 B1 | 4/2002 | Wood |
| 6,502,766 B1 | 1/2003 | Streutker et al. |
| 6,524,475 B1 | 2/2003 | Herrington et al. |
| 6,632,336 B1 * | 10/2003 | Kasuya ........................ 204/271 |
| 6,632,347 B1 * | 10/2003 | Buckley et al. ............. 205/620 |
| 6,736,966 B1 * | 5/2004 | Herrington et al. ......... 210/192 |
| 2002/0175085 A1 | 11/2002 | Harkins |

OTHER PUBLICATIONS

B.B. Gupta et al. "Permeate flux enhancement by pressure and flow pulsations in microfiltration with mineral membranes." Journal of Membrane Science, 70 (1002) 257-266.

L.V. Venczel et al. "Inactivation of Cryptosporidium parvum Oocysts and Clostridium perfringens Spored by a Mixed-Oxidant Disinfectant and by Free Chlorine," Applied and Environmental Microbiology, vol. 63, No. 4 (1997) 1598-1601.

* cited by examiner

ELECTROLYTIC CELL FOR SURFACE AND POINT OF USE DISINFECTION

CROSS-REFERENCE TO RELATED APPLICATIONS

This application claims priority to and the benefit of filing of U.S. Provisional Patent Application Ser. No. 60/448,994, entitled "Electrolytic Cell for Surface and Point of Use Disinfection", filed Feb. 21, 2003. This application is also a continuation-in-part application of U.S. patent application Ser. No. 09/907,092, filed on Jul. 16, 2001, and issued as U.S. Pat. No. 6,736,966 on May 18, 2004, entitled "Portable Water Disinfection System". This application is also related to U.S. Patent Application, entitled "Gas Drive Electrolytic Cell", filed Feb. 23, 2004, and given Ser. No. 10/785,892. The specifications and claims of each application listed are incorporated herein by reference.

FIELD OF THE INVENTION

This invention relates to the production of oxidants in an electrolytic cell that are introduced into an aqueous solution used as a disinfectant or sanitizing liquid.

BACKGROUND OF THE INVENTION

This invention involves electrolytic technology known generally in the art. Electrolytic technology utilizing dimensionally stable anodes (DSA) has been used for years for the production of chlorine and other mixed-oxidant solutions. Dimensionally stable anodes are described in U.S. Pat. No. 3,234,110 to Beer, entitled "Electrode and Method of Making Same". An example of an electrolytic cell with membranes is described in U.S. Pat. No. RE 32,077 to deNora, et al., entitled "Electrode Cell with Membrane and Method for Making Same". An electrolytic cell with dimensionally stable anodes without membranes is described in U.S. Pat. No. 4,761,208 to Gram, et al., entitled "Electrolytic Method and Cell for Sterilizing Water."

The invention also involves the use of electrolytic cells to produce an oxidant. Commercial electrolytic cells have been used routinely for oxidant production that utilizes a flow-through configuration that may or may not be under pressure that is adequate to create flow through the electrolytic device. Examples of cells of this configuration are described in U.S. Pat. No. 6,309,523 to Prasnikar, et al., entitled "Electrode and Electrolytic Cell Containing Same," and U.S. Pat. No. 5,385,711 to Baker, et al., entitled "Electrolytic Cell for Generating Sterilization Solutions Having Increased Ozone Content," and many other membrane-type cells. In other configurations, the oxidant is produced in an open-type cell or drawn into the cell with a syringe or pump-type device, such as described in U.S. Pat. No. 6,524,475 to Herrington, et al., entitled "Portable Water Disinfection System."

The word "sanitize" means: to make sanitary, as by cleaning or sterilizing. The word "disinfect" means: to free from disinfection, esp. by destroying harmful microorganisms; broadly; cleanse. The word "disinfectant" means: a chemical that destroys vegetative forms of harmful microorganisms esp. on inanimate objects but that may be less effective in destroying bacterial spores. Webster's Ninth New Collegiate Dictionary (1984) For purposes of this application, the words sanitize, disinfect, disinfectant and variants thereof are used in the broad sense as meaning, cleanse.

A specific type of electrolytic cell that produces an oxidant is disclosed in U.S. patent application Ser. No. 09/907,092 to Herrington, et al., one of the inventors of the invention described and claimed in this application, entitled "Portable Water Disinfection System," the specification of which is incorporated herein by reference. The specification describes disinfection devices that utilize, in one instance, an electrolytic cell chamber in which hydrogen gas is generated during electrolysis to provide a driving force to expel oxidant from the cell chamber through a pressure-sensitive check valve. In this configuration, unconverted electrolyte is also expelled from the body of the cell as hydrogen gas is generated. In an alternate configuration described in the same application, hydrogen gas pressure is contained in a cell chamber during electrolysis, but the pressure within the cell chamber is limited by the action of a spring loaded piston that continues to increase the volume of the cell chamber as gas volume increases. Ultimately, a valve mechanism opens, and the spring-loaded piston fills the complete volume of the cell chamber forcing the oxidant out of the cell chamber. Another electrolytic cell configuration is disclosed in U.S. patent application Ser. No. 10/785,892, entitled "Gas Drive Electrolytic Cell" filed concurrently herewith. The specification describes a sealed cell during the electrolysis that produces the oxidant which results in a build up of gas pressure, primarily $H_2$ released at the cathode, which overcomes a check valve that opens to expel both the gas and the oxidant.

U.S. Pat. No. 3,996,126 to Rasmussen describes an electrolyzed saline solution generated in a closed container and used to treat teeth and oral cavities. A propellant gas, electrical pump, or manual pump is utilized to force the electrolyzed saline solution out of the container through a tube.

U.S. Pat. No. 4,019,986 to Burris, et al, describes a portable ozone generator and container for purifying water. U.S. Application US 2002/0175085 A1 to Harkins, et al, relates to a stationary electrolyzed oxidizing water system for spraying a sanitizing solution on eggs. U.S. Pat. No. 6,502,766 B1 to Streutker, et al, relates to a motorized sprayer for attachment to a bottle. U.S. Pat. No. 6,363,951 B1 to Wood describes an ozone generation system for use in a water containing device such as a sink for disinfection of materials placed in the sink.

These prior art systems are generally large industrial or commercial apparatus producing large quantities of solution and are therefore not suitable for residential use by consumers. The devices lack portability due to their size as required for a disinfectant or sanitizing solution that may be applied at various locations without the need for pipes or hoses. The prior art does not disclose an apparatus that is low cost, convenient and simple to operate, store, and activate for the production of an oxidant that may be introduced to an aqueous solution which may then be used as a disinfectant for a wide variety of objects.

BRIEF SUMMARY OF THE INVENTION

The present invention comprises an apparatus and method for producing an oxidant to treat a liquid that may be dispensed from a spray bottle or other container as a disinfectant. The apparatus of the invention is low-cost, small and simple, suitable for consumer residential use, although industrial, medical and military applications are also within the scope of the invention. The apparatus may comprise a hand-held portable spray bottle or other container that is initially filled with a liquid, preferably water.

The apparatus further comprises at least one electrolytic cell. The cell includes at least two electrodes, one electrode comprises at least one cathode and another electrode comprises at least one anode. Many types and configurations of electrodes may be suitable for the electrolytic cell of the present invention. The apparatus comprises a control circuit for selectively delivering an electrical charge between the cathode and the anode from any energy source.

The energy source, electrically connected with the control circuit, delivers a controlled electrical charge having a value determined by the cell characteristics, such as the electrolyte type and quantity, size, and other factors. The energy or power source may be a standard or rechargeable battery, direct AC connection or solar power. During generation of oxidants, an electrolyte, preferably comprising a sodium chloride brine solution or a sodium chlorite solution, is located within the cell housing between the anode and cathode. Other oxidants may be produced, based upon the desired application including other halogen oxides, such as chlorine dioxide. The controlled electrical charge passes through the electrolytic solution from cathode to anode, thereby generating at least one oxidant in the electrolyte. A valve or other means may be used to control fluid connection between the cell and the liquid within the container.

In one embodiment, a fluid such as water is placed in the bottle, and oxidants produced within the electrolytic cell are transferred to the water to produce a solution with a free available chlorine concentration of sufficient strength to effectively sanitize the material or surface of an object. In alternative embodiments, the bottle can be an open bottle, closed bottle, or bottle with a spray nozzle or other pumping means to transfer the solution within the bottle to the material or surface to be treated.

In one embodiment of the present invention, the spray bottle is placed on a base unit. The base unit comprises an electrolytic cell, electrolyte storage compartment, power supply, and control circuit. Oxidants produced in the base unit are transferred to the interior of the spray bottle through a valve mechanism. The spray bottle is then removed from the base and used to disinfect surfaces, foods, or other materials requiring sanitization.

In an alternative embodiment of the present invention, the spray bottle includes a handle that houses an electrolytic cell, electrolyte storage compartment, power supply, and control circuit.

In yet another embodiment of the present invention, the spray bottle includes a separate, compact, electrolytic oxidant-producing device or module that removably, mechanically attaches to the spray bottle. In this embodiment, the electrolytic device is used for production of a number of discrete charges of concentrated oxidant and is then replaced when the oxidant production capacity is depleted. The replaceable oxidant producing device comprises an electrolytic cell, electrolyte storage compartment, power supply, and control circuit.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate several embodiments of the present invention and, together with the description, serve to explain the principles of the invention. The drawings are only for the purpose of illustrating several embodiments of the invention and are not to be construed as limiting the invention. In the drawings.

DETAILED DESCRIPTION OF THE INVENTION

Commercial electrolytic cells are in production to produce a mixed-oxidant solution. This process is described in U.S. Pat. No. 4,761,208 and subsequent patents and applications, referred to above, all incorporated herein by reference. The disinfectant produced in this process is very effective for inactivation of microorganisms, particularly microorganisms that are resistant to treatment by conventional chlorine, whether in gas, liquid (sodium hypochlorite), or solid (calcium hypochlorite) form.

Figure 1:
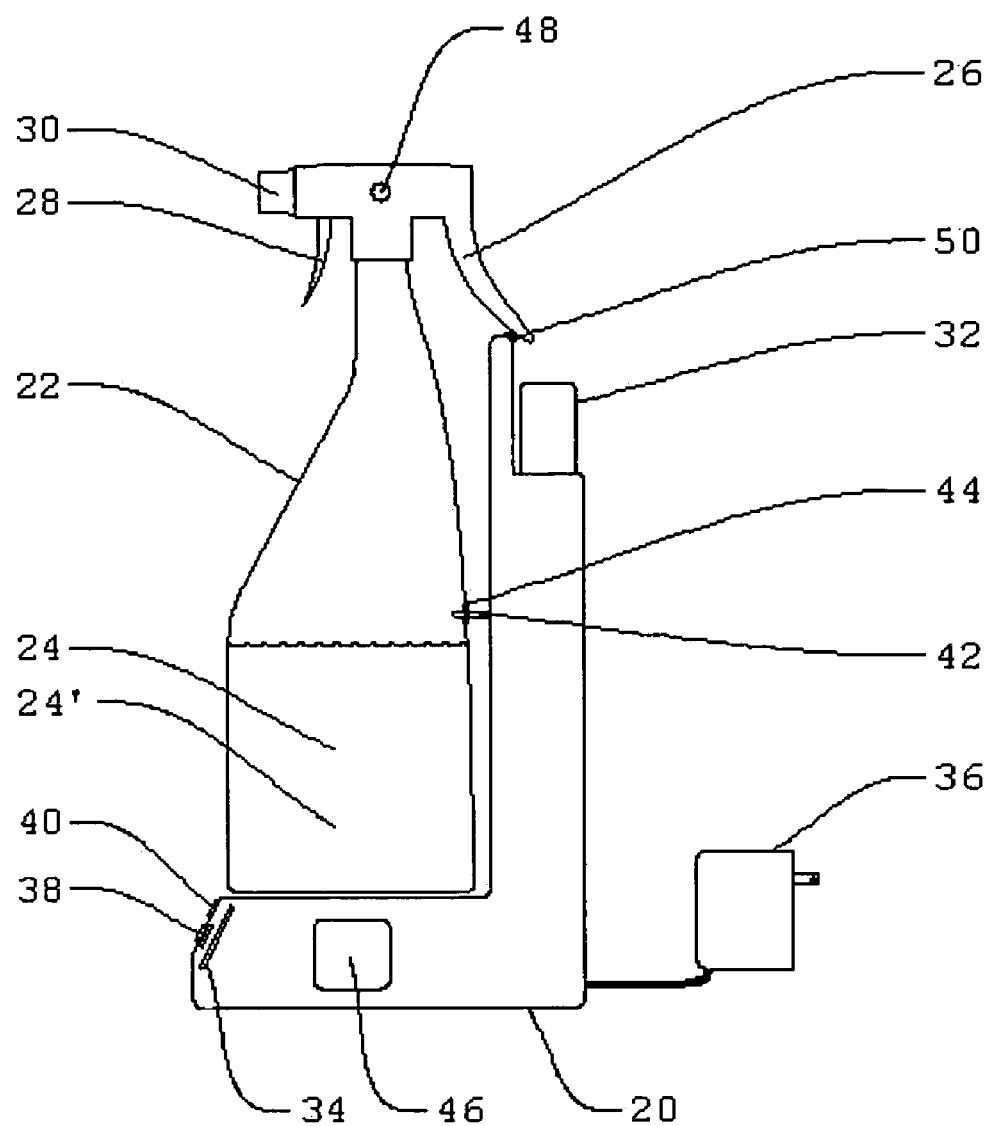
FIG. 1 is a view of a bottle mounted on an oxidant-producing base unit.
Figure 2:
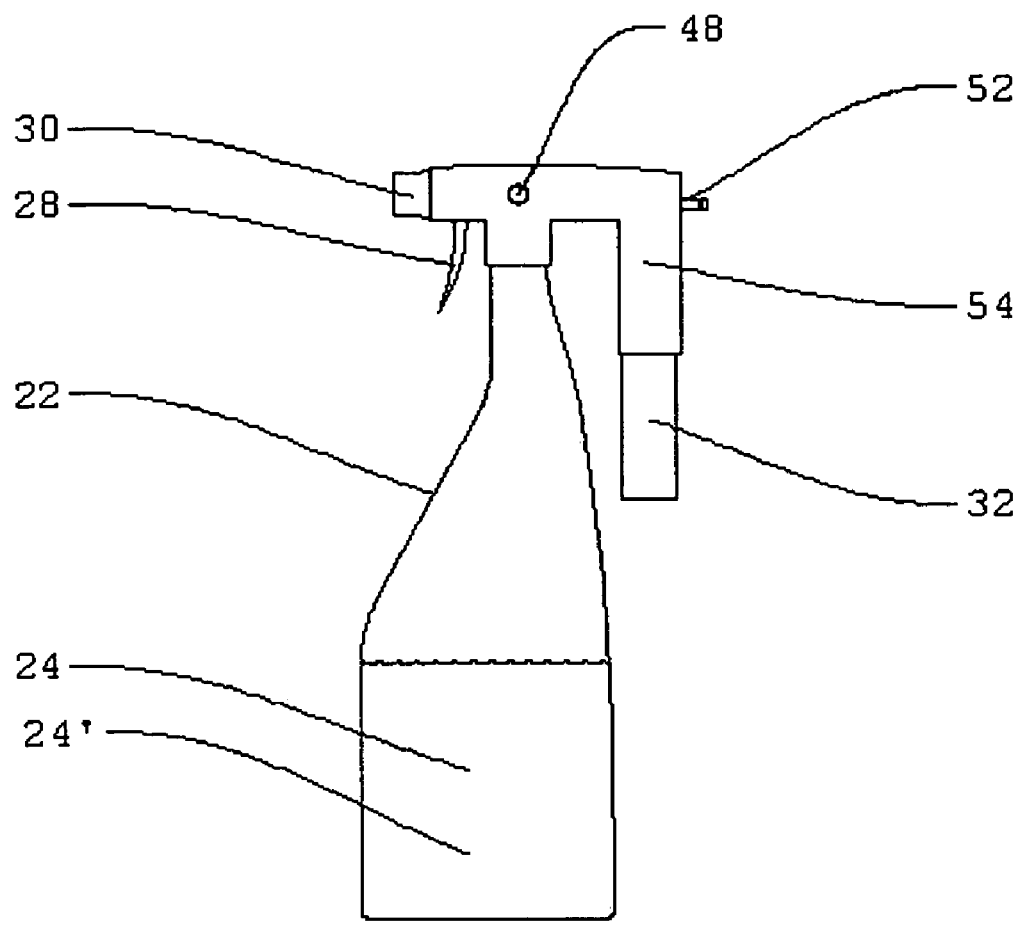
FIG. 2 is a bottle with an oxidant producing unit housed within the handle of the bottle.
Figure 3:
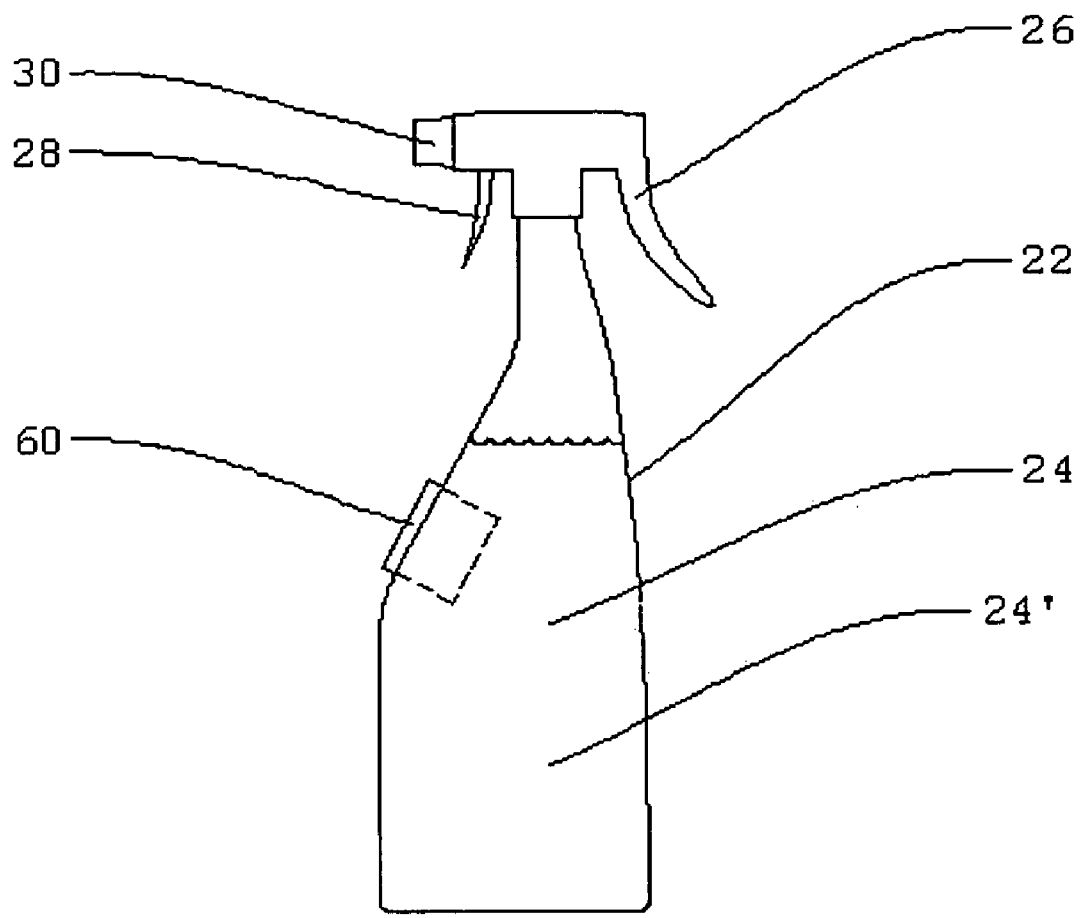
FIG. 3 is a bottle with a separate replaceable oxidant-producing device or module removably attached to the bottle.

A simple version of an oxidant producing device useful in the present invention is described and shown in FIGS. 1, 2, and 3 of U.S. patent application Ser. No. 09/907,092 for "Portable Water Disinfection System", incorporated herein by reference. Another oxidant producing device useful in the present invention is described and shown in U.S. patent application Ser. No. 10/785,892, entitled "Gas Drive Electrolytic Cell", filed concurrently herewith. Other variations and configurations of an electrolytic cell can be produced to accommodate various applications.

The object of the current invention is to incorporate an electrolytic cell into a spray bottle or other container for cleaning solution to enhance the disinfection performance of the cleaning solution. The cleaning solution may have many application including household or industrial surface cleaning (countertops, lavatories, etc), an enhanced cleaning and disinfection solution for washing hands in a sterile environment, for cleaning of medical instruments, and any other application where inactivation of viruses, bacteria, protozoans, molds, spores, volatile organic compounds, pesticides, herbicides, chemical contamination agents, cyanide, and other undesirable matter can be destroyed by the oxidant solution.

Referring to FIG. 1, one embodiment of the present invention comprises base unit 20 with bottle 22 placed on a horizontal surface for receiving the bottle. In this embodiment, bottle 22 comprises a spray bottle. In alternative embodiments of the present invention, the bottle may be a closed or capped bottle, or an open bottle. In the first embodiment, base unit 22 comprises electrolytic cell 46, circuit board 34, and electrolyte storage container 32. In this embodiment, power supply 36 is attached by an electrical cord to base unit 22 and plugs directly into a wall electrical outlet. In an alternative embodiment of the present invention, power supply 36 is located within base unit 22 and plugged directly into an electrical outlet.

In the first embodiment of the present invention, in order to commence operation, fluid 24, preferably water, is introduced into bottle 22. Activation switch 38 is pressed by the user thereby activating production of oxidants. Electrolyte within storage container 32 is transferred to electrolytic cell 46. Electrical power is applied to electrolytic cell 46 through control circuit 34. Status of oxidant production and fault conditions such as low electrolyte levels or other conditions are indicated by illumination of status lights 40. Upon completion of oxidant generation within electrolytic cell 46, oxidants are transferred to the interior of bottle 22 via a valve and probe 42. Probe 42 provides fluid communication with the liquid in bottle 22 via self sealing valve 44 which is integral to bottle 22. Other user controlled apparatus may be employed to transfer the electrolyte to the solution within bottle 22. After oxidants are transferred to the interior of bottle 22, fluid 24' comprises a free available chlorine concentration of sufficient value to sanitize desired objects.

In the first embodiment of the present invention, bottle 22 is removed from base unit 20 and is transported by the user to other locations for the purpose of disinfecting or sanitizing surfaces, food products, or other materials. Bottle 22 comprises handle 26 which further comprises spray trigger 28 and spray nozzle 30. In the first embodiment, handle 22 comprises oxidant efficacy indicator light 48. Oxidant efficacy indicator light 48 provides status to the user of the free available chlorine oxidant strength in fluid 24. Oxidant efficacy indicator light 48 is activated via electrical contact 50. Oxidant efficacy indicator light 48 is powered from a capacitor circuit located within handle 26. In an alternative embodiment, oxidant efficacy indicator light 48 is powered by a battery located within handle 26. In this alternative embodiment, activation of oxidant efficacy indicator light 48 is triggered by a radio frequency signal generated by an RF circuit located within base unit 20.

An alternative embodiment of the present invention is shown in FIG. 2. In this alternative embodiment, the apparatus comprises bottle 22 and sprayer head 54. Sprayer head 54 comprises an electrolytic cell, a power supply, a control circuit, sprayer nozzle 30, spray handle 28, and electrolyte container 32. Sprayer head 54 includes oxidant efficacy indicator light 48. Sprayer head 54 plugs directly into an electrical wall outlet via electrical connector 52 to provide power to recharge a battery located within sprayer head 54. The battery within sprayer head 54 provides the power to deliver a charge to the electrolyte within the electrolytic cell to produce oxidants. In an alternative embodiment, electrolysis within the cell within sprayer head 54 is powered directly from the electrical wall outlet via electrical connectors 52.

Yet another embodiment of the present invention is shown in FIG. 3. In this embodiment, electrolytic cell module 60 comprises an electrolytic cell, electrolyte source, power source, and control circuit. Electrolytic cell module 60 is removable from bottle 22, preferably by threads or other mechanical fluid-tight sealing mechanism to bottle 22. Electrolytic cell module 60 is removable for replacement as a complete assembly from bottle 22. In an alternative embodiment, the electrolyte cell and power source are replaceable components that attach to electrolytic cell module 60. In this embodiment, electrolytic cell module 60 comprises the electrolytic cell and control circuit. The oxidant produced by module 60 is in fluid connection with the liquid in bottle 22.

Applications of the present invention are especially applicable to low-cost water treatment systems for home use by consumers. However, it will be obvious to those versed in the art that this invention can be utilized in a variety of applications including spray bottle applications for surface cleaning, potable water treatment systems, wastewater treatment systems, food cleaning applications, medical instrument sterilization, surgical wards, hospital environments, military medical applications, military chemical and biological weapons decontamination, wound treatment, and other applications where a disinfectant is utilized.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above, and of the corresponding applications, are hereby incorporated by reference.

What is claimed is:

1. An apparatus for delivering a sanitizing solution to a surface, the apparatus comprising:
   an electrolytic cell;
   an electrical power source;
   a circuit which enables the transfer of power from said power source to said electrolytic cell in order to produce at least one oxidant within said electrolytic cell;
   a substantially portable container removable from said electrolytic cell;
   a base for supporting said container, said base comprising said electrolytic cell;
   a connection between said electrolytic cell and said container, wherein said connection enables the at least one oxidant to combine with a substance in the container, thereby forming the sanitizing solution; and
   an opening in said container through which the sanitizing solution is delivered.

2. The apparatus of claim 1 wherein said opening is sealable.

3. The apparatus of claim 1 wherein said container comprises a spray bottle.

4. The apparatus of claim 1 further comprising pumping means.

5. The apparatus of claim 4 wherein said pumping means comprises a handle.

6. The apparatus of claim 4 wherein said connection comprises a valve.

7. The apparatus of claim 4 wherein said valve is opened in response to a pressure of gas produced in said electrolytic cell.

8. The apparatus of claim 4 wherein said connection comprises a fluid-tight seal.

9. The apparatus of claim 4 wherein said pumping means comprises a sprayer head.

10. The apparatus of claim 9 wherein said sprayer head comprises a spray nozzle.

11. The apparatus of claim 1 wherein said base comprises said power source.

12. The apparatus of claim 1 wherein the substance comprises a fluid.

13. The apparatus of claim 12 wherein the fluid comprises an aqueous solution.

14. The apparatus of claim 12 wherein the fluid is water.

15. The apparatus of claim 1 wherein said electrolytic cell utilizes an electrolyte comprising sodium chloride to produce the at least one oxidant.

16. The apparatus of claim 1 wherein said electrolytic cell utilizes an electrolyte comprising sodium chlorite to produce the at least one oxidant.

17. The apparatus of claim 1 wherein said sanitizing solution comprises a free available chlorine concentration of sufficient value to sanitize an object.

18. The apparatus of claim 1 wherein the at least one oxidant comprises at least one member selected from the group consisting of mixed oxidants, chlorine, chlorine dioxide, and combinations thereof.

19. The apparatus of claim 1 further comprising a system activation button and one or more status indicator lights.

20. The apparatus of claim 19 wherein said one or more indicator lights are activated in response to a concentration of free available chlorine in the sanitizing solution.

21. A method of sanitizing a surface, the method comprising the steps of:

providing electrolyte and power to an electrolytic cell;

producing at least one oxidant in the electrolytic cell;

transferring the at least one oxidant to a substance in a substantially portable container, thereby forming a sanitizing solution;

removing the container from a base comprising the electrolytic cell; and delivering the sanitizing solution to the surface.

22. The method of claim 21 wherein the delivering step comprises pumping the sanitizing solution out of the container.

23. The method of claim 21 wherein the delivering step comprises spraying the sanitizing solution on the surface.

24. The method of claim 21 wherein the substance comprises a fluid.

25. The method of claim 24 wherein the fluid comprises an aqueous solution.

26. The method of claim 24 wherein the fluid is water.

27. The method of claim 21 wherein the transferring step comprises opening a valve.

28. The method of claim 27 wherein the valve is opened in response to a pressure of gas produced in the electrolytic cell.

29. The method of claim 21 wherein the providing step comprises charging a battery.

30. The method of claim 21 wherein the providing step comprises replacing a battery.

31. The method of claim 21 wherein the electrolyte comprises sodium chloride.

32. The method of claim 21 wherein the electrolyte comprises sodium chlorite.

33. The method of claim 21 wherein the transferring step comprises raising the free available chlorine concentration of the substance to a value sufficient to sanitize an object.

34. The method of claim 21 wherein the at least one oxidant is selected from the group consisting of mixed oxidants, chlorine, chlorine dioxide, and combinations thereof.

35. The method of claim 21 further comprising monitoring the free available chlorine concentration of the sanitizing solution.

36. The method of claim 21 further comprising the step of transporting the container to the surface.

37. The method of claim 36 further comprising the step of reattaching the container to the electrolytic cell.

38. The method of claim 21 further comprising the step of adding the substance to the container.

39. The method of claim 38 further comprising the step of reattaching the container to the electrolytic cell.

* * * * *